US00PP09001P

United States Patent [19]

Meilland

[11] Patent Number: Plant 9,001

[45] Date of Patent: Dec. 6, 1994

[54] HYBRID TEA ROSE PLANT NAMED MEINIVOZ

[75] Inventor: Alain A. Meilland, Antibes, France

[73] Assignee: The Conard-Pyle Company, West Grove, Pa.

[21] Appl. No.: 151,972

[22] Filed: Nov. 10, 1993

[51] Int. Cl.[5] ..... A01H 5/00
[52] U.S. Cl. ..... Plt./11
[58] Field of Search ..... Plt. 11, 15, 16, 17

*Primary Examiner*—Howard J. Locker

*Attorney, Agent, or Firm*—Burns, Doane, Swecker & Mathis

[57] ABSTRACT

A new and distinct variety of Hybrid Tea rose plant is provided which abundantly and continuously forms attractive very double yellow blossoms. The blossoms are very fragrant and are Amber Yellow in coloration. Such blossoms are long lasting and their petals drop off cleanly. The plant exhibits an upright growth habit, very vigorous vegetation, Bronze Green adult wood, and is particularly well suited for growing in parks and gardens. Also, the new variety is not particularly affected by cryptogamic diseases.

1 Drawing Sheet

SUMMARY OF THE INVENTION

The new variety of Hybrid Tea rose plant was created by artificial pollination wherein two parents were crossed which previously had been studied in the hope that they would contribute the desired characteristics. The female parent (i.e., the seed parent) of the new variety was the product of the crossing of the Meitulandi variety (non-patented in the United States) and the Mischief variety (non-patented in the United States), and the male parent (i.e., the pollen parent) was the Meinuzeten variety (U.S. Plant Pat. No. 4,224). The Meitulandi variety sometimes is known as the Hidalgo variety. The parentage of the new variety can be summarized as folows:

(Meitulandi×Mischief)×Meinuzeten.

The seeds resulting from the above pollination were sown and 52 small plants were obtained which were physically and biologically different from each other. Selective study resulted in the identification of a single plant of the new variety.

It was found that the new variety of Hybrid Tea rose plant of the present invention possesses the following combination of characteristics:

(a) forms in abundance on a continuous basis attractive long-lasting very double fragrant flowers which are Amber Yellow in coloration,
(b) exhibits an upright growth habit,
(c) exhibts very vigorous vegetation,
(d) exhibits Bronze Green adult wood, and
(e) is not particularly affected by cryptogamic diseases.

The petal drop capability of the blooms following flowering is good.

The new variety well meets the needle of the horticultural industry for a number of uses and is particularly well suited for growing as attractive ornamentation in parks and gardens.

The new variety has been found to undergo asexual propagation in France and in the United States by a number of routes, including budding, grafting, and cuttage. The characteristics of the new variety have been found to be strictly transmissible by such asexual propagation from one generation to another.

The new variety has been named the Meinivoz variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were two years of age and were observed during September while budded on *Rosa froebelii* understock and growing outdoors at LeCannet des Maures, Var, France.

FIG. 1 — illustrates a specimen of young shoot;

FIG. 2 — illustrates a specimen of a floral bud before the opening of the sepals;

FIG. 3 — illustrates a specimen of a floral bud at the opening of the sepals;

FIG. 4 — illustrates a specimen of a floral bud at the opening of the petals;

FIG. 5 — illustrates a specimen of a flower in the course of opening;

FIG. 6 — illustrates a specimen of an open flower — plan view — obverse;

FIG. 7 — illustrates a specimen of an open flower — plan view — reverse;

FIG. 8 — illustrates a specimen of a fully open flower — plan view — obverse;

FIG. 9 — illustrates a specimen of a fully open flower — plan view — reverse;

FIG. 10 — illustrates a specimen of a floral receptacle showing the arrangement of the stamens and pistils;

FIG. 11 — illustrates a specimen of a floral receptacle showing the arrangement of the pistils (stamens removed);

FIG. 12 — illustrates a specimen of a flowering stem;

FIG. 13 — illustrates a specimen of a main branch;

FIG. 14 — illustrates specimens of two leaves with three leaflets — plan view — upper surface (right) and under surface (left);

FIG. 15 — illustrates specimens of two leaves with five leaflets — plan view — upper surface (top) and under surface (bottom); and FIG. 16 — illustrates a specimen of a leaf with seven leaflets — plan view — upper surface.

DETAILED DESCRIPTION

Figures 1, 2, 3, 4, 5, 6, 7, 8, 9, 10, 11, 12, 13, 14, 15, 16:
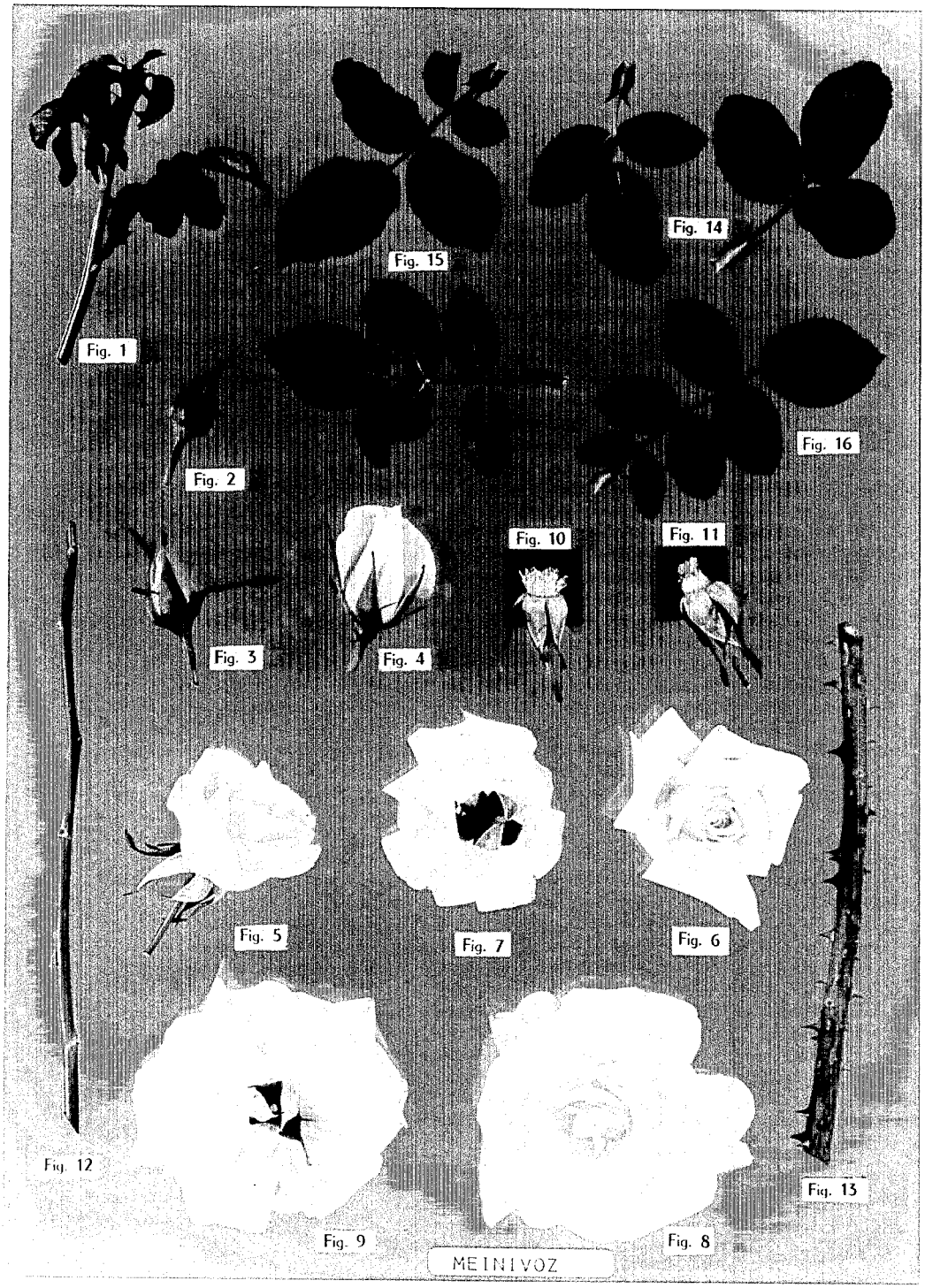

The chart used in the identification of the colors is that of The Royal Horticultural Society (R.H.S. Colour Chart). The description is based on the observation of two-year old plants made during September while budded on *Rosa froebelii* understock and growing outdoors at LeCannet des Maures, Var France. The coloration in common terms precedes reference to the chart.

Class: Hybrid Tea.

Plant:

*Height.*—Approximately 1.2 to 1.3 m. When grown outdoors after one growing season at Wasco, Calif., U.S.A., a mature two-year old plant commonly assumes a height of approximately 1.5 to 1.6 m. Stem lengths of approximately 50 cm. commonly are formed in the springtime when the plant is grown outdoors at Wasco, Calif. U.S.A.

*Habit.*—Upright.

Branches:

*Color.*—Young stems: medium green, Yellow-Green Group 146B, and more or less tinted with reddish coloration. Adult wood: Bronze Green, Yellow-Green Group 146A.

*Thorns.*—Size medium. Quantity: Moderately numerous. Color: Greenish on young stems and light tan on adult wood.

Leaves:

*Stipules.*—Adnate, pectinate, very wide, linear, and edged with pediculate glands.

*Petioles.*—Upper surface: striped reddish green on young foliage and medium green on mature foliage with more or less glandular edges. Under surface: light green, and rarely bears a few prickles.

*Leaflets.*—Number: 3, 5, and 7. Shape: oval. Serration: single and regular. Texture: consistent. General appearance: Matte, dense foliage. Color (young foliage): upper surface: Medium green, Yellow-Green Group 146B. under surface: light green, Yellow-Green Group 147C, and more or less suffused with reddish coloration. Color (adult foliage): upper surface: Bronze Green, Yellow-Green Group 146A. under surface: light green, Yellow-Green Group 146C.

Inflorescence:

*Number of flowers.*—Usually a single bloom per stem.

*Peduncle.*—Light green and smooth. The length is approximately 6 to 8 cm. on average.

*Sepals.*—Upper surface: tomentose, greenish, and more or less stained with reddish coloration. Under surface: light green in coloration, the outer sepals have glandular slightly appendiculated edges, and terminate in a small leaf-like appendix.

*Buds.*—Shape: ovoid. Length: approximately 3 cm. on average. Size: large. Color upon opening: upper surface: Amber Yellow, Yellow-Orange Group 18C. under surface: Amber Yellow, Yellow-Orange Group 18C, suffused with Chinese Coral, Orange-Red Group 32D.

*Flower.*—Shape: cup-like and very double. Diameter: approximately 9 to 10 cm. on average. Color (when opening begins): upper surface: Amber Yellow, Yellow-Orange Group 18C. under surface: Amber Yellow, Yellow-Orange Group 18C, suffused with Chinese Coral, Orange-Red Group 32D. Color (when blooming): upper surface: Amber Yellow, Yellow-Orange Group 18B. under surface: Amber Yellow, Yellow-Orange Group 18B, suffused with Chinese Coral, Orange-Red Group 32D. Color (at end of blooming): Upper surface: Amber Yellow, Yellow-Orange Group 18B widely suffused with Chinese Coral, Orange-Red Group 32D. Also, a color gradient from the center of the flower outwards (as illustrated) commonly is visible wherein the more intense Amber Yellow coloration tends to be more concentrated on the centermost petals. under surface: Amber Yellow, Yellow-Orange Group 18B, widely suffused with Chinese Coral, Orange-Red Group 32D. Frangrance: very strong anise fragrance. Lasting quality: very long lasting when on the plant and when cut and placed in a vase. For instance, typical flowers commonly last about 7 days or more in each instance. Petal number: approximately 40 to 44 on average. Texture: consistent. Petal drop: good. Petal configuration: rounded. Stamen number: approximately 103 to 109 on average. Anthers: normal, bright yellow. Filaments: bright yellow, and of irregular heights. Pistils: approximately 105 to 112 on average. Stigmas: normal, ochre in coloration. Styles: strawlike with fuschia tips, tomentose near the base, and of irregular heights. Receptacle: medium green, and in longitudinal section at the dehiscence of the anthers it is in the shape of a pitcher.

Development:

*Vegetation.*—Very vigorous.

*Blooming.*—Very abundant and continuous throughout the growing season.

*Aptitude to bear fruits.*—Good.

*Resistance to frost.*—Good.

*Resistance to diseases.*—Good.

I claim:

1. A new and distinct variety of the Hybrid Tea rose plant characterized by the following combination of characteristics:

(a) forms in abundance on a continuous basis attractive long-lasting very double fragrant flowers which are Amber Yellow in coloration,
(b) exhibits an upright growth habit,
(c) exhibits very vigorous vegetation,
(d) forms Bronze Green adult wood, and
(e) is not particularly affected by cryptogamic diseases; substantially as herein shown and described.

* * * * *

MEINIVOZ